(12) United States Patent  (10) Patent No.: US 7,499,749 B2
Salo                      (45) Date of Patent: *Mar. 3, 2009

(54) METHOD AND APPARATUS FOR MINIMIZING POST-INFARCT VENTRICULAR REMODELING

(75) Inventor: Rodney W. Salo, Fridley, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 586 days.

This patent is subject to a terminal disclaimer.

(21) Appl. No.: 11/025,847

(22) Filed: Dec. 29, 2004

(65) Prior Publication Data

US 2005/0177195 A1    Aug. 11, 2005

Related U.S. Application Data

(63) Continuation of application No. 10/005,184, filed on Dec. 5, 2001, now Pat. No. 6,973,349.

(51) Int. Cl.
    *A61N 1/00*    (2006.01)
(52) U.S. Cl. .................................................. 607/11
(58) Field of Classification Search ............... 607/9–17; 600/345, 437, 450, 481
    See application file for complete search history.

(56) References Cited

U.S. PATENT DOCUMENTS

| | | |
|---|---|---|
| 4,354,497 A | 10/1982 | Kahn |
| 4,549,548 A | 10/1985 | Wittkampf et al. |
| 4,554,922 A | 11/1985 | Prystowsky et al. |
| 4,628,934 A | 12/1986 | Pohndorf et al. |
| 4,674,518 A | 6/1987 | Salo |
| 4,872,459 A | 10/1989 | Pless et al. |
| 4,880,005 A | 11/1989 | Pless et al. |
| 4,928,688 A | 5/1990 | Mower |
| 5,014,698 A | 5/1991 | Cohen |
| 5,058,605 A | 10/1991 | Slovak |
| 5,109,842 A | 5/1992 | Adinolfi |
| 5,156,149 A | 10/1992 | Hudrlik |
| 5,158,079 A | 10/1992 | Adams et al. |
| 5,174,289 A | 12/1992 | Cohen |
| 5,233,985 A | 8/1993 | Hudrlik |
| 5,267,560 A | 12/1993 | Cohen |

(Continued)

FOREIGN PATENT DOCUMENTS

EP    0522693    1/1993

(Continued)

OTHER PUBLICATIONS

Braunwald, Nina S., et al., "Sustained Paired Electrical Stimuli; Slowing of the Ventricular Rate and Augmentation of Contractile Force", *American Journal of Cardiology*, 14, (1964),pp. 285 & 385-393.

(Continued)

*Primary Examiner*—George Manuel
(74) *Attorney, Agent, or Firm*—Schwegman, Lundberg & Woessner, P.A.

(57) ABSTRACT

A cardiac rhythm management device for in which pre-excitation pacing is applied to one or more sites in proximity to an infarcted region of the ventricular myocardium. Such pacing servers to either prevent or minimize post-infarct remodeling.

19 Claims, 4 Drawing Sheets

U.S. PATENT DOCUMENTS

| | | |
|---|---|---|
| 5,331,768 A | 7/1994 | Takeuchi |
| 5,370,665 A | 12/1994 | Hudrlik |
| 5,514,161 A | 5/1996 | Limousin |
| 5,534,016 A | 7/1996 | Boute |
| 5,584,867 A | 12/1996 | Limousin et al. |
| 5,674,259 A | 10/1997 | Gray |
| 5,683,429 A | 11/1997 | Mehra |
| 5,792,203 A | 8/1998 | Schroeppel |
| 5,797,970 A | 8/1998 | Pouvreau |
| 5,824,019 A | 10/1998 | Rueter et al. |
| 5,851,226 A | 12/1998 | Skubitz et al. |
| 5,935,160 A | 8/1999 | Auricchio et al. |
| 5,995,871 A | 11/1999 | Knisley |
| 6,038,483 A | 3/2000 | KenKnight et al. |
| 6,058,329 A | 5/2000 | Salo et al. |
| 6,066,094 A | 5/2000 | Ben-Haim |
| 6,112,117 A | 8/2000 | KenKnight et al. |
| 6,151,524 A | 11/2000 | Krig et al. |
| 6,152,955 A | 11/2000 | KenKnight et al. |
| 6,223,082 B1 | 4/2001 | Bakels et al. |
| 6,285,898 B1 | 9/2001 | Ben-Haim |
| 6,363,279 B1 | 3/2002 | Ben-Haim et al. |
| 6,574,506 B2 * | 6/2003 | Kramer et al. ............ 607/9 |
| 6,628,988 B2 * | 9/2003 | Kramer et al. ............ 607/9 |
| 6,640,135 B1 | 10/2003 | Salo et al. |
| 6,915,160 B2 | 7/2005 | Auricchio et al. |
| 6,965,797 B2 * | 11/2005 | Pastore et al. ............ 607/17 |
| 6,973,349 B2 | 12/2005 | Salo |
| 7,020,521 B1 | 3/2006 | Brewer et al. |
| 7,215,997 B2 | 5/2007 | Yu et al. |
| 2002/0002389 A1 | 1/2002 | Bradley et al. |
| 2002/0091415 A1 | 7/2002 | Lovett et al. |
| 2003/0014083 A1 | 1/2003 | Kupper |
| 2003/0023278 A1 | 1/2003 | Pastore et al. |
| 2003/0105493 A1 | 6/2003 | Salo |
| 2003/0153952 A1 | 8/2003 | Auricchio et al. |
| 2003/0187482 A1 | 10/2003 | Pastore et al. |
| 2004/0030357 A1 | 2/2004 | Salo et al. |
| 2004/0044374 A1 | 3/2004 | Weinberg et al. |
| 2004/0049236 A1 | 3/2004 | Kramer et al. |
| 2004/0054381 A1 | 3/2004 | Pastore et al. |
| 2004/0098057 A1 | 5/2004 | Pastore |
| 2005/0065568 A1 | 3/2005 | Liu et al. |
| 2005/0137631 A1 | 6/2005 | Yu et al. |
| 2005/0216066 A1 | 9/2005 | Auricchio et al. |
| 2007/0162081 A1 | 7/2007 | Yu et al. |

FOREIGN PATENT DOCUMENTS

| | | |
|---|---|---|
| WO | WO-9725098 A1 | 7/1997 |
| WO | WO-99/10042 | 3/1999 |
| WO | WO-00/09206 | 2/2000 |
| WO | WO-0004947 A2 | 2/2000 |
| WO | WO-0108748 A2 | 2/2001 |
| WO | WO-0130436 A2 | 5/2001 |
| WO | WO-01/76689 | 10/2001 |
| WO | WO-02/087694 | 11/2002 |
| WO | WO-02087694 A1 | 11/2002 |

OTHER PUBLICATIONS

Sabbah, Hani N., et al., "Delivery of Non-Excitatory Contractility-Modulation Electric Signals Improve Left Ventricular Performance in Dogs with Heart Failure", *Circulation, Supplement 1*, 100 (18), Abstract No. 631, (Nov. 2, 1999),pp. 1-122.

Watanabe, Michiko, et al., "Developmental Remodeling and Shortening of Cardiac Outflow Tract Involves Myocyte Programmed Cell Death", *Development*, 125 (19), (1998),3809-3820.

Yu, Yinghong, "Dynamic Device Therapy Control for Treating Post Myocardial Infarction Patients", U.S. Appl. No. 10/744,900, filed Dec. 22, 2003, 37 pgs.

Reiter, Michael J., et al., "Electrophysiological Effects of Acute Dilatation in the Isolated Rabbit Hear", *Circulation*, vol. 96, No. 11, (Dec. 2, 1997),4050-4056.

Auricchio, "Cardiac Resynchronization Therapy Restores Optimal Atrioventricular Mechanical Timing in Heart Failure Patients with Ventricular Conduction Delay", *Journal of the American College of Cardiology*, vol. 39, No. 7, (Apr. 3, 2002),1163-1169.

Min, Mart, "Electrical Impedance and Cardiac Monitoring-Technology, Potential and Applications", *International Journal of Bioelectromagnetism*, 5(1), (2003),53-56.

Sheiban, I., et al., "Time course and determinants of left ventricular function recovery after primary angioplasty in patients with acute myocardial infarction", *J Am Coll Cardiol.*, 38(2), (Aug. 2001),464-71.

* cited by examiner

METHOD AND APPARATUS FOR MINIMIZING POST-INFARCT VENTRICULAR REMODELING

CROSS-REFERENCE TO RELATED APPLICATION

This application is a continuation of U.S. patent application Ser. No. 10/005,184, filed on Dec. 5, 2001, now issued as U.S. Pat. No. 6,973,349, the specification of which is incorporated herein by reference.

FIELD OF THE INVENTION

This invention pertains to cardiac rhythm management devices such as pacemakers and other implantable devices.

BACKGROUND

A myocardial infarction is the irreversible damage done to a segment of heart muscle by ischemia, where the myocardium is deprived of adequate oxygen and metabolite removal due to an interruption in blood supply. It is usually due to a sudden thrombotic occlusion of a coronary artery, commonly called a heart attack. If the coronary artery becomes completely occluded and there is poor collateral blood flow to the affected area, a transmural or full-wall thickness infarct can result in which much of the contractile function of the area is lost. Over a period of one to two months, the necrotic tissue heals, leaving a scar. The most extreme example of this is a ventricular aneurysm where all of the muscle fibers in the area are destroyed and replaced by fibrous scar tissue.

Even if the ventricular dysfunction as a result of the infarct is not immediately life-threatening, a common sequela of a transmural myocardial infarction in the left ventricle is heart failure brought about by ventricular remodeling. Heart failure refers to a condition where cardiac output falls below a level adequate to meet the metabolic needs of the body which, if uncompensated, leads to rapid death. One physiological compensatory mechanism that acts to increase cardiac output is the increased diastolic filling pressure of the ventricles as an increased volume of blood is left in the lungs and venous system. This increases the preload, which is the degree to which the ventricles are stretched by the volume of blood in the ventricles at the end of diastole. An increase in preload causes an increase in stroke volume during systole, a phenomena known as the Frank-Starling principle.

Left ventricular remodeling is a physiological process in response to the hemodynamic effects of the infarct that causes changes in the shape and size of the left ventricle. Remodeling is initiated in response to a redistribution of cardiac stress and strain caused by the impairment of contractile function in the infarcted area as well as in nearby and/or interspersed viable myocardial tissue with lessened contractility due to the infarct. FIG. 1 illustrates three stages of the remodeling process following a transmural infarction in the apical region of the left ventricle. Stage A is the acute phase which lasts only for a few hours. The infarcted area labeled INF at this stage includes tissue undergoing ischemic necrosis and is surrounded by normal myocardium labeled NML. Until scar tissue forms, the infarcted area is particularly vulnerable to the distending forces within the ventricle and undergoes expansion over a period of hours to days as shown at stage B. Over the next few days and months after scar tissue has formed, global remodeling and chamber enlargement occur as shown at stage C due to complex alterations in the architecture of the left ventricle involving both infarcted and non-infarcted areas. Remodeling is thought to be the result of a complex interplay of hemodynamic, neural, and hormonal factors.

The ventricular dilation resulting from the increased preload causes increased ventricular wall stress at a given systolic pressure in accordance with Laplace's law. Along with the increased pressure-volume work done by the ventricle, this acts as a stimulus for compensatory hypertrophy of the ventricular myocardium. Hypertrophy can increase systolic pressures but, if the hypertrophy is not sufficient to meet the increased wall stress, further and progressive dilation results. This non-compensatory dilation causes wall thinning and further impairment in left ventricular function. It also has been shown that the sustained stresses causing hypertrophy may induce apoptosis (i.e., programmed cell death) of cardiac muscle cells. Thus, although ventricular dilation and hypertrophy may at first be compensatory and increase cardiac output, the process ultimately results in further deterioration and dysfunction. It has been found that the extent of left ventricular remodeling in the late period after an infarction, as represented by measurements of end-systolic and end-diastolic left ventricular volumes, is an even more powerful predictor of subsequent mortality than the extent of coronary artery disease. Preventing or minimizing such post-infarct remodeling is the primary concern of the present invention.

SUMMARY

The present invention relates to a method and apparatus for minimizing the ventricular remodeling that normally occurs after a myocardial infarction using pacing therapy. The part of the myocardium that is most vulnerable to the post-infarct remodeling process is the infarct region, which is an area that includes sites in and around the infarct where the myocardial fibers are still intact but contractile function is impaired. The infarct region is thus the area most likely to undergo the progressive non-compensatory dilation described above with wall thinning and further impairment of function. By pacing sites in proximity to the infarct with appropriately timed pacing pulses, the infarct region is pre-excited in a manner that lessens the mechanical stress to which it is subjected, thus reducing the stimulus for remodeling. Decreasing the wall stress of the infarct region also lessens the probability of an arrhythmia arising from the region. Another advantage obtained with resynchronizing the ventricular contraction by pre-exciting a weakened infarct region is a hemodynamically more efficient contraction.

DETAILED DESCRIPTION

Figure 1C:
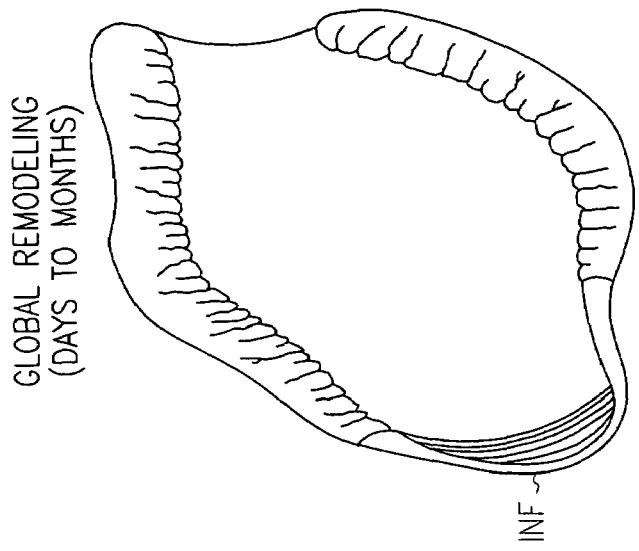
FIG. 1 illustrates the stages of remodeling after a myocardial infarction.
Figure 1B:
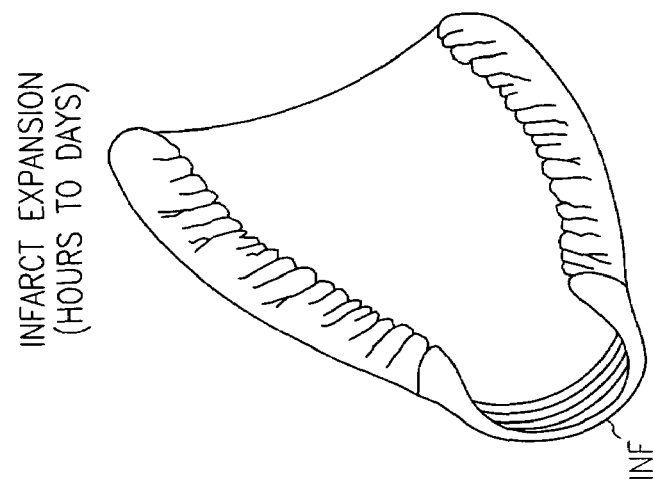
Figure 1A:
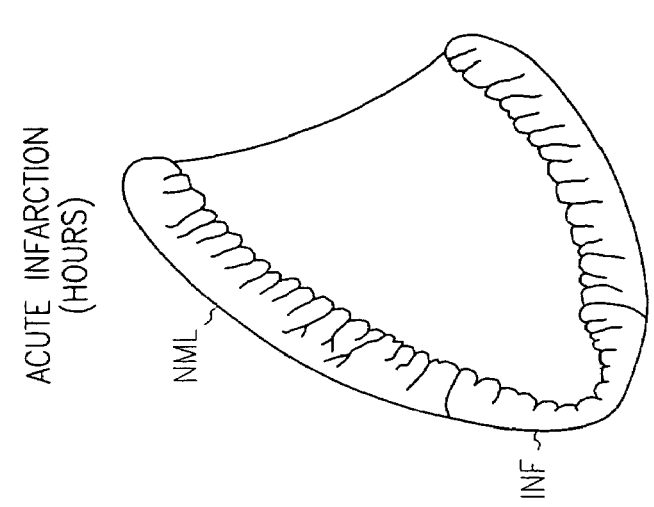

When a transmural myocardial infarction in the left ventricle occurs, the affected area suffers a loss of contractile fibers that depends upon the degree of collateral circulation to the area. For example, the infarction may either leave a non-contractile scar or leave some viable myocardium interspersed with scar tissue, with the myocardial fibers that surround the infarcted area suffering a variable amount of destruction. In any case, regions in and around the infarct suffer impaired contractility, and it is this impairment that is responsible for the ventricular dysfunction that initiates the remodeling process as described above. Whether the infarction results in a non-contractile scar or a fibrous region with diminished contractility, the viable myocardium in proximity to the infarct are the regions of the ventricle that are least able to respond to the increased stresses brought about by ventricular dysfunction in a physiologically appropriate manner. These regions are thus the parts of the ventricle that are most vulnerable to the post-infarct remodeling process. If a way could be found to subject the regions in proximity the infarct to lessened mechanical stress without unduly compromising ventricular systolic function, the undesirable remodeling of the region could be prevented or minimized.

The degree to which a heart muscle fiber is stretched before it contracts is termed the preload, while the degree of tension or stress on a heart muscle fiber as it contracts is termed the afterload. The maximum tension and velocity of shortening of a muscle fiber increases with increasing preload, and the increase in contractile response of the heart with increasing preload is known as the Frank-Starling principle. When a myocardial region contracts late relative to other regions, the contraction of those other regions stretches the later contracting region and increases its preloading, thus causing an increase in the contractile force generated by the region. Conversely, a myocardial region that contracts earlier relative to other regions experiences decreased preloading and generates less contractile force. Because pressure within the ventricles rises rapidly from a diastolic to a systolic value as blood is pumped out into the aorta and pulmonary arteries, the parts of the ventricles that contract earlier during systole do so against a lower afterload than do parts of the ventricles contracting later. Thus, if a ventricular region can be made to contract earlier than parts of the ventricle, it will be subjected to both a decreased preload and afterload which decreases the mechanical stress experienced by the region relative to other regions. The region will also do less work thus lessening its metabolic demands and the degree of any ischemia that may be present.

In accordance with the present invention, electrostimulatory pacing pulses are delivered to one or more sites in or around the infarct in a manner that pre-excites those sites relative to the rest of the ventricle. (As the term is used herein, a pacing pulse is any electrical stimulation of the heart of sufficient energy to initiate a propagating depolarization, whether or not intended to enforce a particular heart rate.) In a normal heartbeat, the specialized His-Purkinje conduction network of the heart rapidly conducts excitatory impulses from the sino-atrial node to the atrio-ventricular node, and thence to the ventricular myocardium to result in a coordinated contraction of both ventricles. Artificial pacing with an electrode fixed into an area of the myocardium does not take advantage of the heart's normal specialized conduction system for conducting excitation throughout the ventricles because the specialized conduction system can only be entered by impulses emanating from the atrio-ventricular node. Thus the spread of excitation from a ventricular pacing site must proceed only via the much slower conducting ventricular muscle fibers, resulting in the part of the ventricular myocardium stimulated by the pacing electrode contracting well before parts of the ventricle located more distally to the electrode. This pre-excitation of a paced site relative to other sites can be used to deliberately change the distribution of wall stress experienced by the ventricle during the cardiac pumping cycle. Pre-excitation of the infarct region relative to other regions unloads the infarct region from mechanical stress by decreasing its afterload and preload, thus preventing or minimizing the remodeling that would otherwise occur. In addition, because the contractility of the infarct region is impaired, pre-excitation of the region results in a resynchronized ventricular contraction that is hemodynamically more effective. This is beneficial in reducing the stimulus for remodeling and reducing the incidence of angina due to coronary insufficiency. Decreasing the wall stress of the infarct region also lessens its oxygen requirements and lessens the probability of an arrhythmia arising in the region.

Pacing therapy to unload the infarct region may be implemented by pacing the ventricles at a single site in proximity to the infarct region or by pacing at multiple ventricular sites in such proximity. In the latter case, the pacing pulses may be delivered to the multiple sites simultaneously or in a defined pulse output sequence. As described below, the single-site or multiple site pacing may be performed in accordance with a bradycardia pacing algorithm such as an inhibited demand mode or a triggered mode.

Figure 2:
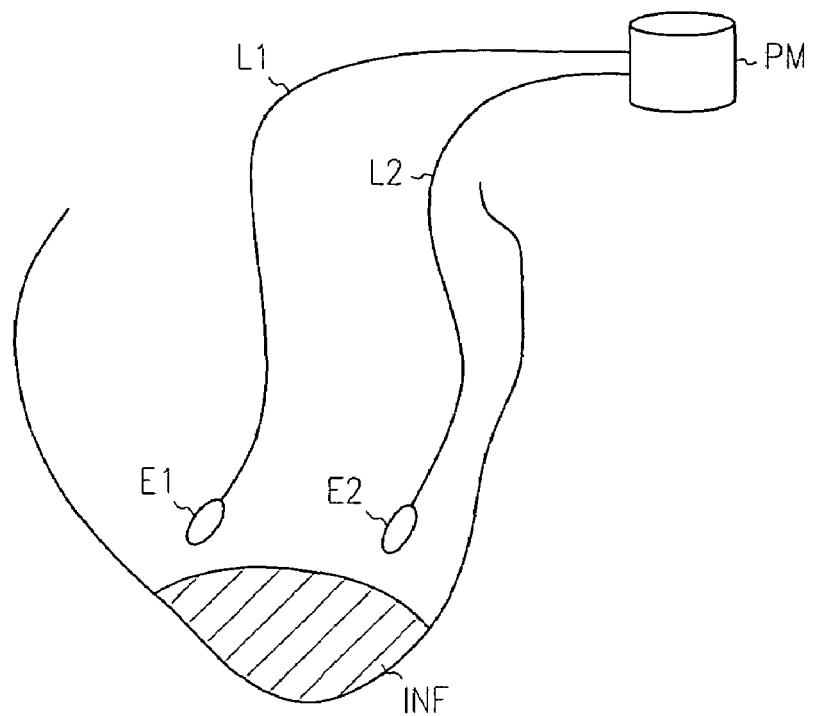
FIG. 2 illustrates a pacemaker and an exemplary pacing configuration.
Figure 3:
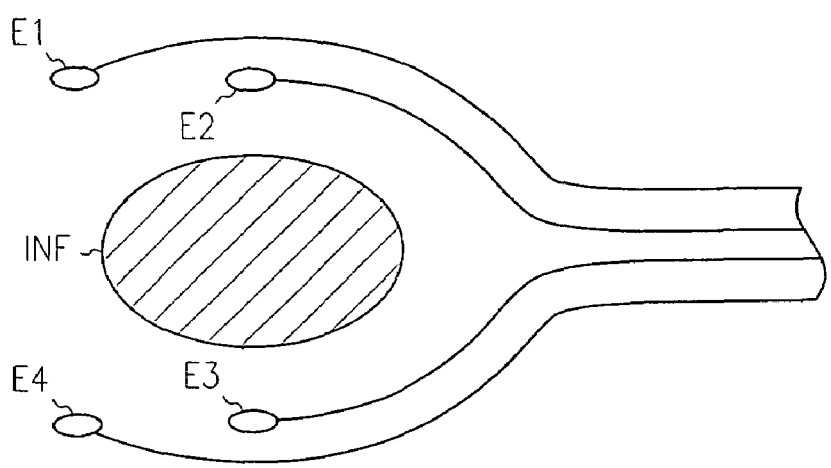
FIG. 3 illustrates a multi-site electrode arrangement.
Figure 4A:
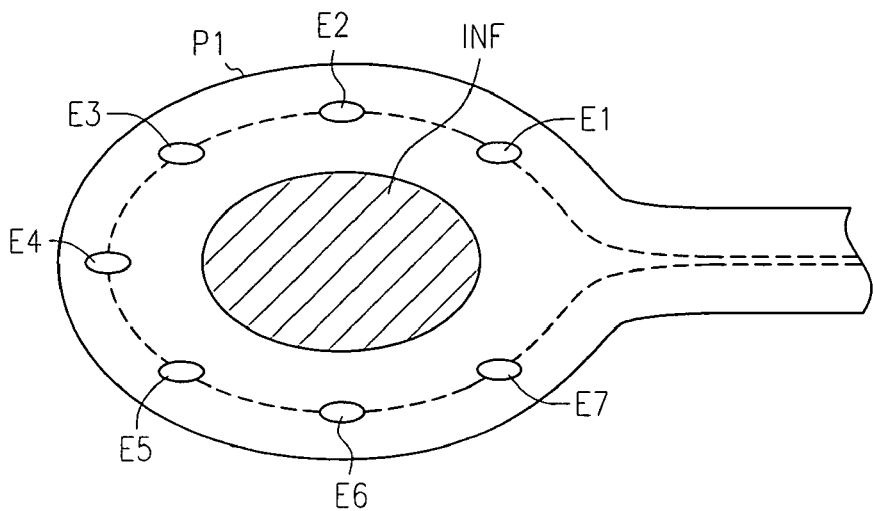
FIGS. 4A through 4C illustrate examples of patch electrodes for multi-site pacing.
Figure 4B:
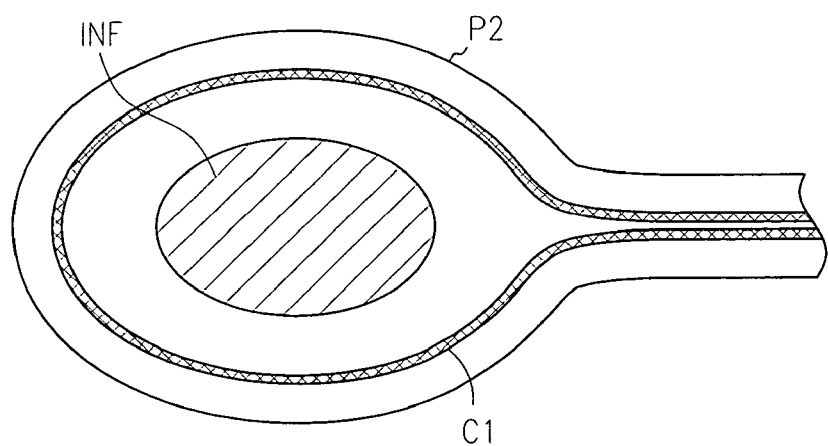
Figure 4C:
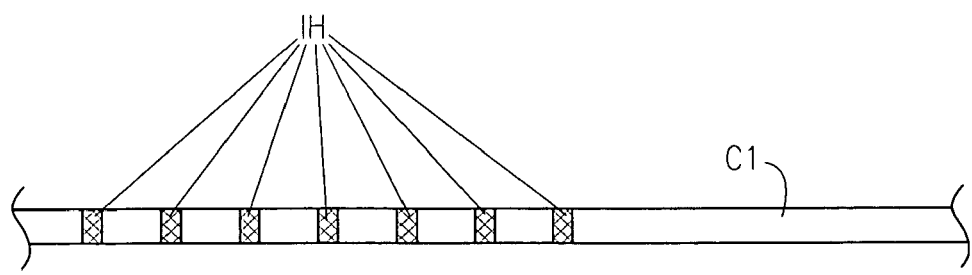

In order to pre-excite the infarct region, one or more pacing electrodes must be placed in proximity to the region. The area of the infarct can be identified by a number of means, including ultrasonic imaging, PET scans, thallium scans, and MRI perfusion scans. In the case of a left ventricular infarct, epicardial leads can either be placed directly on the epicardium with a thoracotomy (an open chest surgical operation) or a thorascopic procedure, or leads can be threaded from the upper venous system into a cardiac vein via the coronary sinus. (See, e.g., U.S. Pat. No. 5,935,160 issued to Auricchio et al., and assigned to Cardiac Pacemakers, Inc., which is hereby incorporated by reference.) FIG. 2 is an exemplary depiction of two such leads L1 and L2 that are passed from a pacemaker PM through cardiac veins in the epicardium of the left ventricle so that the pacing electrodes E1 and E2 are disposed adjacent to the infarct region INF. In the case of lead placement by a thoracotomy or thorascopic procedure, it is possible to dispose the electrodes in a manner that more precisely circumscribes or overlies the infarct region. FIG. 3 shows an example of multiple electrodes E1 through E4 placed around the infarct region INF, where the electrodes may either be connected to the pacemaker by a single lead or separate leads for each electrode. FIG. 4A shows another example of an electrode arrangement where the multiple electrodes E1 through E7 are incorporated into a patch P1 so as to surround or overlay the infarct region INF. FIG. 4B shows another example of a patch P2 in which the electrode is a single continuous conductor C1 that is designed to surround the infarct region. FIG. 4C shows an exemplary construction of the conductor C1 where areas on the outer surface of the conductor are intermittently coated with an insulating material IM so as to increase the current density at the uncoated regions when the conductor is energized. Such a higher current density may be necessary in some cases to excite a myocardial region which has been rendered less excitable by ischemia.

A block diagram of an exemplary pacemaker for delivering pre-excitation pacing therapy to a site or sites in proximity to an infarct as described above is illustrated in FIG. 5. Pacemakers are usually implanted subcutaneously on the patient's chest, and are connected to sensing/pacing electrodes by leads either threaded through the vessels of the upper venous system to the heart or by leads that penetrate the chest wall. (As the term is used herein, a "pacemaker" should be taken to mean any cardiac rhythm management device with a pacing functionality regardless of any other functions it may perform.) The controller of the pacemaker is made up of a microprocessor 10 communicating with a memory 12 via a bidirectional data bus, where the memory 12 typically comprises a ROM (read-only memory) for program storage and a RAM (random-access memory) for data storage. The controller could be implemented by other types of logic circuitry (e.g., discrete components or programmable logic arrays) using a state machine type of design, but a microprocessor-based system is preferable. The controller is capable of operating the pacemaker in a number of programmed modes where a programmed mode defines how pacing pulses are output in response to sensed events and expiration of time intervals. A telemetry interface 80 is also provided for communicating with an external programmer.

Figure 5:
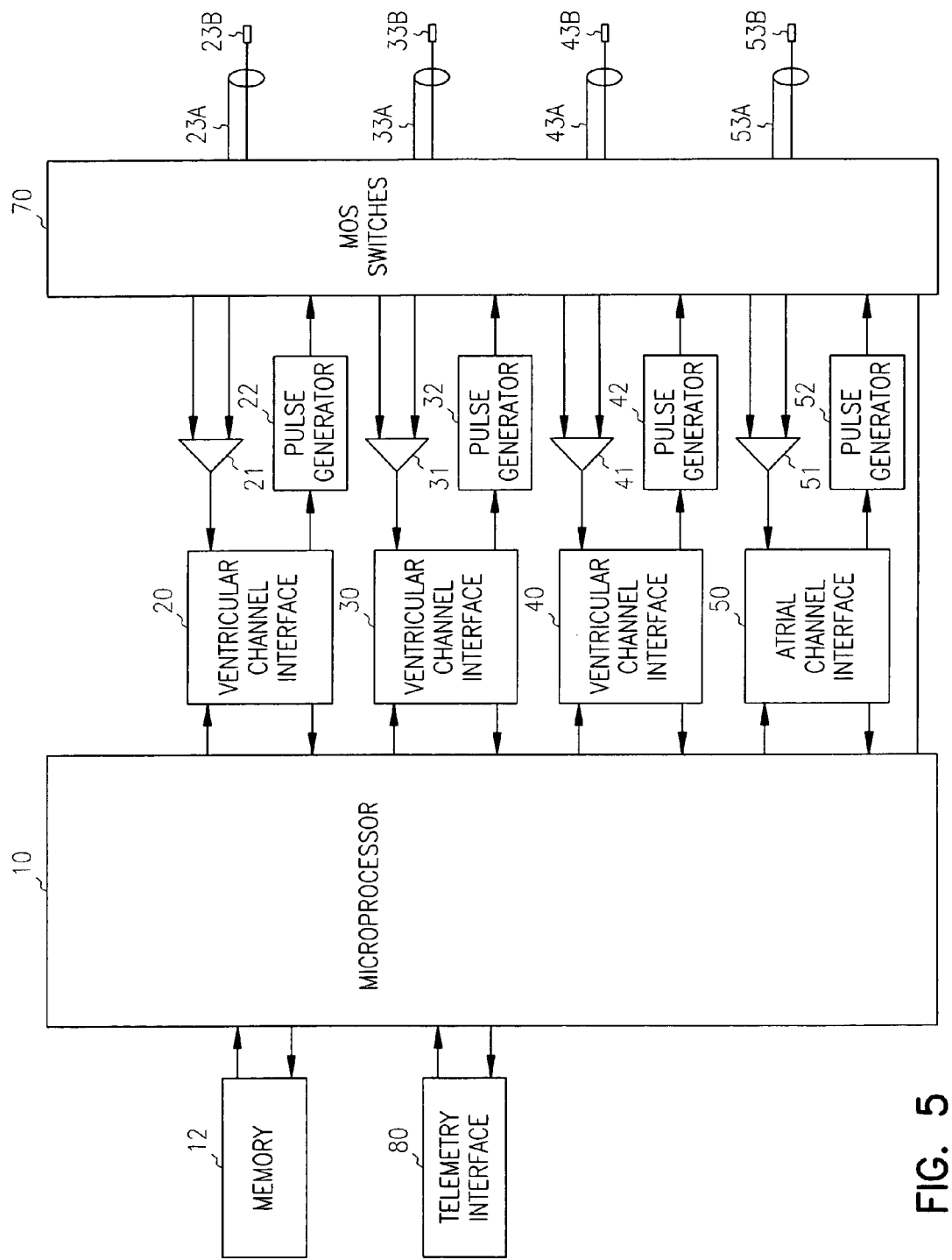
FIG. 5 is a block diagram of an exemplary cardiac rhythm management device for delivering pre-excitation pacing.

The device illustrated in FIG. 5 has multiple sensing and pacing channels and is therefore capable of delivering single-site or multiple site ventricular pacing. The multiple sensing and pacing channels may be configured as either atrial or ventricular channels allowing the device to deliver such pacing with or without atrial tracking. Shown in FIG. 5 is a configuration with one atrial sensing/pacing channel and three ventricular sensing/pacing channels. The atrial sensing/pacing channel comprises ring electrode 53a, tip electrode 53b, sense amplifier 51, pulse generator 52, and an atrial channel interface 50 which communicates bidirectionally with a port of microprocessor 10. The three ventricular sensing/pacing channels that include ring electrodes 23a, 33a, and 43a, tip electrodes 23b, 33b, and 43b, sense amplifiers 21, 31, and 41, pulse generators 22, 32, and 42, and ventricular channel interfaces 20, 30, and 40. A pacing channel is made up of the pulse generator connected to the electrode while a sensing channel is made up of the sense amplifier connected to the electrode. The channel interfaces include analog-to-digital converters for digitizing sensing signal inputs from the sensing amplifiers, registers that can be written to for adjusting the gain and threshold values of the sensing amplifiers, and registers for controlling the output of pacing pulses and/or changing the pacing pulse amplitude. In certain patients, pacing of sites in proximity to an infarct or within ischemic regions may be less excitable than normal and require an increased pacing energy in order to achieve capture (i.e., initiating of a propagating action potential). For each channel, the same electrode pair can be used for both sensing and pacing. In this embodiment, bipolar leads that include two electrodes are used for outputting a pacing pulse and/or sensing intrinsic activity. Other embodiments may employ a single electrode for sensing and pacing in each channel, known as a unipolar lead. A MOS switching network 70 controlled by the microprocessor is used to switch the electrodes from the input of a sense amplifier to the output of a pulse generator.

The controller 10 controls the overall operation of the device in accordance with programmed instructions stored in memory. The controller 10 interprets electrogram signals from the sensing channels and controls the delivery of paces in accordance with a pacing mode. The sensing circuitry of the pacemaker generates atrial and ventricular electrogram signals from the voltages sensed by the electrodes of a particular channel. When an electrogram signal in an atrial or sensing channel exceeds a specified threshold, the controller detects an atrial or ventricular sense, respectively, which pacing algorithms may employ to trigger or inhibit pacing.

Pre-excitation pacing of one or more ventricular sites in proximity to an infarct may be delivered with a bradycardia pacing mode, which refers to a pacing algorithm that enforces a certain minimum heart rate. Pacemakers can enforce a minimum heart rate either asynchronously or synchronously. In asynchronous pacing, the heart is paced at a fixed rate irrespective of intrinsic cardiac activity. Because of the risk of inducing an arrhythmia with asynchronous pacing, most pacemakers for treating bradycardia are programmed to operate synchronously in a so-called demand mode where sensed cardiac events occurring within a defined interval either trigger or inhibit a pacing pulse. Inhibited demand pacing modes utilize escape intervals to control pacing in accordance with sensed intrinsic activity. In an inhibited demand ventricular pacing mode, the ventricle is paced during a cardiac cycle only after expiration of a defined escape interval during which no intrinsic beat by the chamber is detected. For example, a ventricular escape interval can be defined between ventricular events so as to be restarted with each ventricular sense or pace. The inverse of this escape interval is the minimum rate at which the pacemaker will allow the ventricles to beat, sometimes referred to as the lower rate limit (LRL). In an atrial tracking pacing mode, another ventricular escape interval is defined between atrial and ventricular events, referred to as the atrio-ventricular interval (AVI). The atrio-ventricular interval is triggered by an atrial sense and stopped by a ventricular sense or pace. A ventricular pace is delivered upon expiration of the atrio-ventricular interval if no ventricular sense occurs before the expiration. Because it is only paced beats that pre-excite the infarct region, it may be desirable in certain patients to decrease the AVI to be below the intrinsic PR interval (i.e., the normal time for an intrinsic ventricular beat to occur after an atrial sense) or increase the LRL to be slightly above the patient's normal resting heart rate.

In the case where the pre-excitation pacing of the ventricle is delivered at multiple sites, the sites may be paced simultaneously or in accordance with a particular pulse output sequence that specifies the order in which the sites are to be paced during a single beat. As aforesaid, one of the benefits of pre-excitation pacing of the infarct region is resynchronization of the contraction that results in hemodynamic improvement. In some patients, such resynchronization may be more successful if multiple ventricular sites are paced in a specified sequence such that certain of the pacing sites are pre-excited earlier than others during a single beat.

It was noted above that another benefit of pre-exciting ventricular tissue during systole is a reduction in its oxygen requirements, thus preventing or alleviating ischemia in the infarct region. Pre-excitation pacing as described above may also be employed to unload ischemic regions in either the atria or ventricles that are not associated with an infarct, which may act to prevent the development of angina in the patient or a subsequent infarct. Ischemic regions, whether or not associated with an infarct, can be identified with an angiogram, thallium scan or an MRI perfusion scan, and sites within ischemic regions so identified can be selected as pacing sites.

In a further refinement, pre-excitation pacing therapy may be started, stopped, or modified based upon sensor measurements. For example, the pacemaker could measure the impedance between pairs of electrodes to detect wall motion or changes in wall thickness during the cardiac cycle. Separate pairs of electrodes can be used to produce impedance signals from both a paced region and a non-ischemic region, such as the right ventricle if the paced and ischemic region is in the left ventricle. Ischemia in the paced region can then be monitored by comparing the timing of the contraction in the paced region with the timing of the non-ischemic region. If the contractions in the paced region is delayed or significantly prolonged, an increase in ischemia can be surmised, and pre-excitation pacing to the area can either be started or increased. Conversely, if a decrease in ischemia is detected, pre-excitation pacing may either be stopped or reduced. Modifications to the pacing therapy can also be made in accordance with detected changes in the wall thickness of the paced region. In another embodiment, an accelerometer or microphone on the pacing lead or in the device package may be used to sense the acoustic energy generated by the heart during a cardiac cycle. Changes in the amplitude or morphology of the acoustic energy signal may then be used to infer changes in the wall motion and the efficiency of contraction and relaxation. The applied pre-excitation pacing therapy can then be modified based upon this information. (See U.S. Pat. No. 6,058,329, hereby incorporated by reference.)

A device for delivering pre-excitation pacing therapy as described above may also have other functionality that can be of benefit to patients with ischemic heart disease, such as cardioversion/defibrillation. Drug delivery capability incorporated into the device may also be useful. FIG. 5 shows a drug delivery system interfaced to the microprocessor which may take various forms. For example, to improve the efficacy of the pre-excitation therapy in preventing or minimizing remodeling, it may be desirable to simultaneously treat the patient with ACE (angiotensin converting enzyme) inhibitors or beta-blockers. It may also be useful to deliver biological agents such as growth factors or anti-apoptotic factors directly to the infarct region. Such delivery may be implemented by infusing the agent through a lumen in a pacing lead that is disposed near the infarct.

Although the invention has been described in conjunction with the foregoing specific embodiments, many alternatives, variations, and modifications will be apparent to those of ordinary skill in the art. Other such alternatives, variations, and modifications are intended to fall within the scope of the following appended claims.

What is claimed is:

1. A cardiac rhythm management device for delivering pre-excitation pacing therapy to minimize ventricular remodeling, comprising:
   one or more sensing channels for sensing intrinsic cardiac activity;
   a plurality of pacing channels for delivering pacing pulses;
   a patch having incorporated therein one or more electrodes on the periphery of the patch so as to circumscribe a selected myocardial region when the patch is placed thereon;
   a controller for controlling the delivery of pacing pulses in accordance with a pacing mode, wherein the controller is programmed to deliver the pacing pulses to one or more electrodes of the patch in a manner that pre-excites the circumscribed region.

2. The device of claim 1 wherein the patch has incorporated therein a conductor located on the periphery of the patch so as to circumscribe the selected myocardial region when the patch is placed thereon.

3. The device of claim 2 wherein areas on the outer surface of the conductor are intermittently coated with an insulating material so as to increase the current density at uncoated regions when the conductor is energized.

4. The device of claim 1 further comprising a drug delivery system for delivering an agent selected from a group consisting of an ACE inhibitor, a beta blocker, a growth factor, and an anti-apoptotic factor.

5. The device of claim 1 further comprising an impedance sensor for detecting changes in wall motion and wall thickness in an area in proximity to the selected myocardial region and wherein the controller is programmed to modify the delivery of pacing pulses in accordance therewith.

6. The device of claim 1 further comprising an acoustic sensor for sensing acoustic energy generated by the heart during a cardiac cycle and wherein the controller is programmed to modify the delivery of pacing pulses in accordance therewith.

7. The device of claim 1 wherein the controller is programmed to deliver pacing pulses in an inhibited demand ventricular pacing mode.

8. The device of claim 1 wherein the controller is programmed to deliver pacing pulses an atrial tracking mode.

9. The device of claim 1 wherein the controller is programmed to deliver pacing pulses to multiple sites in proximity to the selected myocardial region simultaneously.

10. The device of claim 1 wherein the controller is programmed to deliver pacing pulses to multiple sites in proximity to the selected myocardial region in an order defined by a specified pulse output sequence.

11. A method for minimizing ventricular remodeling, comprising:
    identifying an area in a ventricle that is vulnerable to remodeling;
    disposing a patch having electrodes at the periphery thereof so as to circumscribe a region in proximity to the vulnerable area;
    delivering pacing pulses to one or more sites in proximity to the vulnerable area via one or more electrodes of the patch; and,
    wherein the pacing pulses are delivered in a manner that pre-excites the site or sites in proximity to the vulnerable area relative to other areas of the ventricle.

12. The method of claim 11 wherein the pacing pulses are delivered in accordance with a bradycardia pacing mode.

13. The method of claim 12 wherein the pacing mode is an inhibited demand ventricular pacing mode.

14. The method of claim 12 wherein the pacing mode is an atrial tracking mode.

15. The method of claim 11 wherein paces are delivered to multiple sites in proximity to the vulnerable area simultaneously.

16. The method of claim 11 wherein paces are delivered to multiple sites in proximity to the vulnerable area in an order defined by a specified pulse output sequence.

17. The method of claim 11 further comprising modifying the delivery of pacing pulses in accordance with impedance sensor measurements that indicate ventricular wall motion or thickness.

18. The method of claim 11 wherein the site or sites to which pacing pulses are delivered are located in the left ventricle.

19. The method of claim 18 wherein the site or sites are paced with one or more electrodes disposed in a cardiac vein.

* * * * *